United States Patent
Manus et al.

(10) Patent No.: US 11,058,617 B2
(45) Date of Patent: Jul. 13, 2021

(54) METHODS

(71) Applicant: Colgate-Palmolive Company, New York, NY (US)

(72) Inventors: Lisa Manus, Lawrenceville, NJ (US); Michael Stranick, Bridgewater, NJ (US); Donghui Wu, Bridgewater, NJ (US)

(73) Assignee: Colgate-Palmolive Company, New York, NY (US)

( * ) Notice: Subject to any disclaimer, the term of this patent is extended or adjusted under 35 U.S.C. 154(b) by 0 days.

(21) Appl. No.: 16/713,732

(22) Filed: Dec. 13, 2019

(65) Prior Publication Data

US 2020/0197271 A1 Jun. 25, 2020

Related U.S. Application Data

(60) Provisional application No. 62/782,838, filed on Dec. 20, 2018.

(51) Int. Cl.
| | | |
|---|---|---|
| *A61K 8/27* | (2006.01) | |
| *A61K 8/44* | (2006.01) | |
| *A61K 8/362* | (2006.01) | |
| *A61Q 11/00* | (2006.01) | |

(52) U.S. Cl.
CPC .............. *A61K 8/27* (2013.01); *A61K 8/362* (2013.01); *A61K 8/44* (2013.01); *A61Q 11/00* (2013.01)

(58) Field of Classification Search
CPC combination set(s) only.
See application file for complete search history.

(56) References Cited

U.S. PATENT DOCUMENTS

| | | | |
|---|---|---|---|
| 9,486,396 B2 | 11/2016 | Maloney et al. | |
| 9,585,827 B2 | 3/2017 | Stephenson | |
| 10,058,493 B2 | 8/2018 | Manus et al. | |
| 10,342,750 B2 | 7/2019 | Prencipe et al. | |
| 10,617,620 B2 | 4/2020 | Prencipe et al. | |
| 10,744,077 B2 | 8/2020 | Manus et al. | |
| 2009/0202454 A1 | 8/2009 | Mello et al. | |
| 2010/0047191 A1* | 2/2010 | Fowler | A61K 8/19 424/52 |
| 2013/0071456 A1 | 3/2013 | Fruge et al. | |
| 2015/0313813 A1 | 11/2015 | Rege et al. | |
| 2016/0000664 A1* | 1/2016 | Dehghan | A61K 8/19 424/52 |
| 2017/0020795 A1 | 1/2017 | Maloney et al. | |
| 2017/0209489 A1 | 7/2017 | Geibel | |
| 2017/0224595 A1 | 8/2017 | Xu et al. | |
| 2017/0348550 A1* | 12/2017 | Josias | A61K 8/44 |
| 2018/0015016 A1 | 1/2018 | Huang et al. | |
| 2018/0021234 A1 | 1/2018 | Prencipe et al. | |
| 2019/0038531 A1 | 2/2019 | Rege et al. | |
| 2019/0269586 A1 | 9/2019 | Prencipe et al. | |
| 2020/0009031 A1 | 1/2020 | Prencipe et al. | |
| 2020/0206116 A1 | 7/2020 | Prencipe et al. | |

FOREIGN PATENT DOCUMENTS

TW 201625201 7/2020

OTHER PUBLICATIONS

T. Yilmaz, M. Demir Bajin, R.Önder Günaydin, S. Özer, T. Sözen. Laryngopharyngeal reflux and Helicobacter pylori. World J. Gastroenterol. Jul. 21, 20141; 20(27): 8964-8970. (Year: 2014).*
International Search Report and the Written Opinion of the International Searching Authority issued in International Application PCT/US2019/066225 dated Mar. 20, 2020.
TW201625201A, Colgate Palmolive Co., "Dentifrice comprising zinc—amino acid complex and phosphates," Jul. 16, 2016, English language machine translation of abstract, Espacenet, date obtained: Aug. 17, 2020, 1 page <https://worldwide.espacenet.com/patent/search/family/051134461/publication/TW201625201A?q=TW%20201625201>.
Baig et al., 2014, "Protective effects of SnF2—Part I. Mineral solubilization studies on powdered apatite," Int. Dental Journal 64(Suppl. 1):4-10.
Mohammed et al., 2014, "Physical chemical effects of zinc on in vivo enamel demineralization," Journal of Dentistry 42:1096-1104.
Mohammed et al., 2015, "Inhibitory effects of zinc ions on enamel demineralization kinetics in vitro," Caries Research 49(6):600-605.
Phan et al., 2015, "Gastric hypersecretory states: Investigation and management," Current Treatment Options Gastroenterology 13(4):386-397.

* cited by examiner

*Primary Examiner* — Michael P Cohen

(57) ABSTRACT

Provided herein are methods of treating one or more symptoms of a gastric disorder in the oral cavity of a subject in need thereof, wherein the method comprises applying to the subject's teeth an oral care composition comprising a basic amino acid in free or salt form, wherein the basic amino acid is arginine (e.g., free form arginine); zinc oxide and zinc citrate; and an orally acceptable carrier.

8 Claims, No Drawings

METHODS

CROSS REFERENCE TO RELATED APPLICATIONS

This application claims priority to U.S. Provisional Application No. 62/782,838, filed on Dec. 20, 2018, the contents of which are incorporated herein by reference in its entirety.

FIELD

This invention relates to methods of treating symptoms pertaining to gastric disorders, comprising the application of oral care compositions comprising arginine or salt thereof, zinc oxide and zinc citrate, and an orally acceptable carrier, to a subject's tooth; as well as to methods of using, methods of identification of novel candidate compounds, and compounds for use.

BACKGROUND

Dental enamel is a thin, hard layer of calcified material that covers the crown of teeth. The major mineral component of dental enamel is hydroxyapatite, a crystalline form of calcium phosphate. Chemical erosion of dental enamel may arise from tooth exposure to acidic food and drinks (extrinsic) or to stomach acids (intrinsic) arising from gastric reflux. The erosion of dental enamel can lead to enhanced tooth sensitivity due to increased exposure of the dentin tubules and increased dentin visibility leading to the appearance of more yellow teeth. The salivary pellicle (a thin layer of salivary glycoproteins deposited on teeth) is integral in protecting the teeth against an erosive challenge. As a result, people that experience xerostomia are more susceptible to acid erosion damage.

The sustained presence of intrinsic acid in the oral cavity can be damaging to the enamel of the tooth. In some cases, regurgitation of stomach acids following meals, especially after overeating, can be considered normal, for up to about 1 hour a day. However, for people with certain gastric disorders, such as gastroesophageal reflux disease (GERD), the intrusion of gastric acids into the oral cavity for prolonged periods of time and during, for example sleep, is especially damaging to the teeth, as salivation and swallowing are reduced, and, in a supine position, the lower molars can be bathed in the acids.

Zinc is a well-known antimicrobial agent used in toothpaste compositions. Zinc is also a well-known essential mineral for human health, and has been reported to help strengthen dental enamel and to promote cell repair. However, formulations with zinc have a variety of challenges. Unfortunately, conventional toothpaste formulations often require a high concentrations of zinc, e.g., 2% by weight or more, to achieve efficacy. And, at this concentration, the zinc imparts a notably astringent taste to the composition.

Consequently, there is still the need to provide improved methods of using oral care compositions to protect tooth enamel from the effects of intrinsic stomach acid erosion.

BRIEF SUMMARY

The present inventors have unexpectedly found that combinations of a basic amino acid (i.e., arginine) and one or more sources of zinc (i.e., zinc oxide and zinc citrate, e.g., zinc citrate trihydrate), are effective in inhibiting or decreasing calcium release in tooth enamel exposed to acid. Without being bound by theory, it is believed that these compositions have beneficial effects in inhibiting, repairing, or mitigating the effects of dental erosion.

In the Examples listed herein, the inventors have detailed how toothpaste slurries with the combination of arginine, zinc oxide and zinc citrate are effective in inhibiting or limiting the amount calcium that is released from Calcium-deficient HA powder upon exposure to citric acid. As noted below, Calcium-deficient HA is chosen to mimic calcium-phosphate material given its similarity in structure, and elemental composition, to dental enamel. Citric acid is also an excellent chelating agent, binding metals by making them soluble. Given citric acid's ability to act as a potent chelator, the ability of the Test Formulation toothpaste slurries described in the Examples—containing arginine, zinc oxide and zinc citrate—to limit or inhibit calcium release is all the more impressive.

Without being bound by theory, the ability to limit or inhibit calcium release, under such acid conditions described herein, demonstrates how the methods described herein can be effective in treating symptoms (e.g., tooth enamel loss) that occur when gastric disorders (e.g., GERD, heartburn, indigestion) result in the elevation (or prolonged presence) of gastric acid in the oral cavity.

Accordingly, in one aspect, the present invention relates to a method (Method 1.0) of treating one or more symptoms of a gastric disorder in the oral cavity of a subject in need thereof, wherein the method comprises applying to the subject's teeth an oral care composition comprising:
 a. Basic amino acid in free or salt form, wherein the basic amino acid is arginine (e.g., free form arginine);
 b. zinc oxide and zinc citrate;
 c. an orally acceptable carrier.

For example, Method 1.0 comprises:
1.1 Method 1.0, wherein the one or more symptoms the gastric disorder is dental erosion (e.g., tooth enamel erosion) that is consequent to the presence of gastric acid (e.g., stomach acid) in the oral cavity (e.g., increased or elevated amounts of gastric acid).
1.2 Method 1.1, wherein the dental erosion (e.g., erosion of the tooth enamel) that is consequent to the presence of gastric acid is the erosion of the subject's tooth enamel from loss of calcium.
1.3 Any of the preceding methods, wherein the oral care composition inhibits or decreases the release of calcium from the subject's tooth enamel.
1.4 Any of the preceding methods, wherein the in the inhibition or decrease of the release of calcium in the subject's tooth enamel is relative to a reference standard.
1.5 Any of the preceding, wherein the oral care composition inhibits the release of calcium relative to one or more oral care compositions that do not contain zinc.
1.6 Any of the preceding methods, wherein the gastric disorder increases the amount of gastric acid in the oral cavity (e.g., relative to a reference standard).
1.7 Any of the preceding methods, wherein the gastric disorder prolongs the period which gastric acid is present in a subject's oral cavity (e.g., relative to a reference standard).
1.8 Any of the preceding methods, wherein the subject has a gastric disorder that increases the amount of gastric acid in the oral cavity of the subject (and/or prolongs the oral cavity to exposure of gastric acid), and wherein the gastric disorder is selected from the group consisting of: duodenal ulcers, gastric ulcers, gastroesophageal reflux disease (GERD), erosive esophagitis, gastroesophageal reflux disease weakly reactive (poorly responsive symptomatic gastroesophageal reflux disease), bulimia nervosa, pathological gastrointestinal hypersecretory disease (pathological gastrointestinal hypersecretory disease), Zhuo-Ellison syndrome, heartburn, and acid indigestion.

1.9 Method of 1.7, wherein the gastric disorder is gastroesophageal reflux disease (GERD).

1.10 Any of the preceding methods, wherein the one or more symptoms is that the subject is exposed to gastric acids in the oral cavity during sleep.

1.11 Any of the preceding methods, further comprising wherein the subject is at risk for dental erosion.

1.12 Method of 1.11, wherein the risk for dental erosion is selected from the group consisting of xerostomia, hypersensitivity, weakened tooth integrity (e.g., from one or more tooth fractures), and where the subject has tooth discoloration.

1.13 Any of the preceding methods, wherein the amount of gastric acid in the oral cavity is elevated relative to a reference standard.

1.14 Any of the preceding methods, wherein the basic amino acid has the L-configuration (e.g., L-arginine).

1.15 Any of the preceding methods, wherein the arginine is in free form.

1.16 Any of the preceding methods, wherein the basic amino acid is provided in the form of a di- or tri-peptide comprising arginine, or salts thereof.

1.17 Any of the preceding methods, wherein the arginine is present in an amount corresponding to 1% to 15%, e.g., 3 wt. % to 10 wt. % of the total composition weight, about e.g., 1.5%, 4%, 5%, or 8%, wherein the weight of the basic amino acid is calculated as free form.

1.18 Any of the preceding methods, wherein the arginine is present in an amount from 0.1 wt. %-6.0 wt. %. (e.g., about 1.5 wt %).

1.19 Any of the preceding methods, wherein the arginine is present in an amount of about 1.5 wt. %.

1.20 Any of the preceding methods, wherein the amino acid is L-arginine.

1.21 Any of the preceding methods, wherein the amino acid is free form arginine.

1.22 Any of the preceding methods, wherein the amino acid is arginine phosphate.

1.23 Any of the preceding methods, wherein the amino acid is arginine hydrochloride.

1.24 Any of the preceding methods, wherein the amino acid is arginine bicarbonate.

1.25 Any of the preceding methods, wherein the amino acid is arginine ionized by neutralization with an acid or a salt of an acid.

1.26 Any of preceding methods, wherein the composition is ethanol-free.

1.27 Any of the preceding methods, wherein the composition further comprising a fluoride source selected from: stannous fluoride, sodium fluoride, potassium fluoride, sodium monofluorophosphate, sodium fluorosilicate, ammonium fluorosilicate, amine fluoride (e.g., N'-octadecyltrimethylendiamine-N,N,N'-tris(2-ethanol)-dihydrofluoride), ammonium fluoride, titanium fluoride, hexafluorosulfate, and combinations thereof.

1.28 Any of the preceding methods, wherein the fluoride source is sodium fluoride.

1.29 Any of the preceding methods, wherein the fluoride source is a fluoride salt present in an amount of 0.1 wt. % to 2 wt. % (0.1 wt %-0.6 wt. %) of the total composition weight (e.g., sodium fluoride (e.g., about 0.32 wt. %).

1.30 Any of the preceding methods, wherein the fluoride source is a soluble fluoride salt which provides fluoride ion in an amount of from 50 to 25,000 ppm (e.g., 750-2000 ppm, e.g., 1000-1500 ppm, e.g., about 1000 ppm, e.g., about 1450 ppm)

1.31 Any of the preceding methods, wherein the fluoride source is sodium fluoride which provides fluoride in an amount from 750-2000 ppm (e.g., about 1450 ppm)

1.32 Any of the preceding methods, wherein the fluoride source is sodium fluoride and which provides fluoride in an amount from 1000 ppm -1500 ppm.

1.33 Any of the preceding methods, wherein the fluoride source is sodium fluoride and which provides fluoride in an amount of about 1450 ppm.

1.34 Any of the preceding methods, wherein the pH is between 7.5 and 10.5, e.g., 8-9.5, e.g., 7.2-9.0, about 8.0, about 9.0.

1.35 Any of the preceding methods, further comprising calcium carbonate and/or precipitated calcium carbonate.

1.36 Any of the preceding methods, further comprising an effective amount of one or more alkali phosphate salts, e.g., sodium, potassium or calcium salts, e.g., selected from alkali dibasic phosphate and alkali pyrophosphate salts, e.g., alkali phosphate salts selected from sodium phosphate dibasic, potassium phosphate dibasic, dicalcium phosphate dihydrate, calcium pyrophosphate, tetrasodium pyrophosphate, tetrapotassium pyrophosphate, sodium tripolyphosphate, disodium hydrogenorthophoshpate, monosodium phosphate, pentapotassium triphosphate and mixtures of any of two or more of these, e.g., in an amount of 0.1-20%, e.g., 0.1-8%, e.g., 0.2 to 5%, e.g., 0.3 to 2%, e.g., 0.3 to 1%, e.g about 0.5%, about 1%, about 2%, about 5%, about 6%, by weight of the composition.

1.37 Any of the preceding methods, comprising tetrapotassium pyrophosphate, disodium hydrogenorthophoshpate, monosodium phosphate, and pentapotassium triphosphate.

1.38 Any of the preceding methods, wherein the composition comprises a polyphosphate.

1.39 The methods of 1.26, wherein the polyphosphate is tetrasodium pyrophosphate.

1.40 The composition of 1.39, wherein the tetrasodium pyrophosphate is from 0.1-1.0 wt % (e.g., about 0.5 wt %).

1.41 Any of the preceding methods, wherein the composition further comprises an abrasive or particulate (e.g., silica).

1.42 Any of the preceding methods, wherein the silica is synthetic amorphous silica (e.g., 1% -28% by wt.) (e.g., 8%-25% by wt.).

1.43 Any of the preceding methods, wherein the silica abrasives are silica gels or precipitated amorphous silicas, e.g. silicas having an average particle size ranging from 2.5 microns to 12 microns.

1.44 Any of the preceding methods, further comprising a small particle silica having a median particle size (d50) of 1-5 microns (e.g., 3-4 microns) (e.g., about 5 wt. % Sorbosil AC43 from PQ Corporation, Warrington, United Kingdom).

1.45 Any of the preceding methods, wherein 20-30 wt % of the total silica in the composition is small particle silica (e.g., having a median particle size (d50) of 3-4 microns) and wherein the small particle silica is about 5 wt. % of the oral care composition.

1.46 Any of the preceding methods, comprising silica wherein the silica is used as a thickening agent, e.g., particle silica.

1.47 Any of the preceding methods, wherein the composition further comprises a nonionic surfactant, wherein the nonionic surfactant is in an amount of from 0.5-5%, e.g, 1-2%, selected from poloxamers (e.g., poloxamer 407), polysorbates (e.g., polysorbate 20), polyoxyl hydrogenated castor oil (e.g., polyoxyl 40 hydrogenated castor oil), and mixtures thereof.

1.48 Method of 1.47, wherein the poloxamer nonionic surfactant has a polyoxypropylene molecular mass of from 3000 to 5000 g/mol and a polyoxyethylene content of from 60 to 80 mol %, e.g., the poloxamer nonionic surfactant comprises poloxamer 407.

1.49 Any of the preceding methods, wherein the ratio of the amount of zinc oxide (e.g., wt. %) to zinc citrate (e.g., wt %) in the composition is from 1.5:1 to 4.5:1 (e.g., 2:1, 2.5:1, 3:1, 3.5:1, or 4:1).

1.50 Any of the preceding methods, wherein the zinc citrate is in an amount of from 0.25 to 1.0 wt % (e.g., 0.5 wt. %) and zinc oxide in the composition may be present in an amount of from 0.75 to 1.25 wt % (e.g., 1.0 wt. %) based on the weight of the oral care composition.

1.51 Any of the preceding methods wherein the zinc citrate is about 0.5 wt %.

1.52 Any of the preceding methods wherein the zinc oxide is about 1.0 wt %.

1.53 Any of the preceding methods where the zinc citrate is about 0.5 wt % and the zinc oxide is about 1.0 wt %.

1.54 Any of the preceding methods wherein the benzyl alcohol is present from 0.1-0.6 wt %., (e.g., 0.1-0.4 wt %) e.g. about 0.1 wt. %, about 0.2 wt. %, or about 0.3 wt. %.

1.55 Any of the preceding methods wherein the benzyl alcohol is about 0.1 wt %.

1.56 Any of the preceding methods wherein benzyl alcohol is present at is considered a preservative.

1.57 Any of the preceding methods, wherein the composition comprises polymer films.

1.58 Any of the preceding methods, wherein the composition comprises a flavoring, fragrance and/or a coloring agent.

1.59 The method of 1.58, wherein the flavoring agent is sodium saccharin, sucralose, or a mixture thereof.

1.60 Any of the preceding methods, wherein the composition comprises a thickening agent selected from the group consisting of carboxyvinyl polymers, carrageenan, xanthan, hydroxyethyl cellulose and water soluble salts of cellulose ethers (e.g., sodium carboxymethyl cellulose and sodium carboxymethyl hydroxyethyl cellulose).

1.61 Any of the preceding methods, wherein the composition comprises sodium carboxymethyl cellulose (e.g., from 0.5 wt. %-1.5 wt. %).

1.62 Any of the preceding methods, wherein the oral care composition comprises from 5%-40%, e.g., 10%-35%, e.g., about 15%, 25%, 30%, and 35% water.

1.63 Any of the preceding methods, wherein the oral care composition comprises an additional antibacterial agent selected from: herbal extracts and essential oils (e.g., rosemary extract, tea extract, magnolia extract, thymol, menthol, eucalyptol, geraniol, carvacrol, citral, hinokitol, catechol, methyl salicylate, epigallocatechin gallate, epigallocatechin, gallic acid, miswak extract, sea-buckthorn extract), bisguanide antiseptics (e.g., chlorhexidine, alexidine or octenidine), quaternary ammonium compounds (e.g., cetylpyridinium chloride (CPC), benzalkonium chloride, tetradecylpyridinium chloride (TPC), N-tetradecyl-4-ethylpyridinium chloride (TDEPC)), phenolic antiseptics, hexetidine, octenidine, sanguinarine, povidone iodine, delmopinol, salifluor, metal ions (e.g., zinc salts, for example, Zinc Chloride, Zinc Lactate, Zinc Sulfate, stannous salts, copper salts, iron salts), sanguinarine, propolis and oxygenating agents (e.g., hydrogen peroxide, buffered sodium peroxyborate or peroxycarbonate), phthalic acid and its salts, monoperthalic acid and its salts and esters, ascorbyl stearate, oleoyl sarcosine, alkyl sulfate, dioctyl sulfosuccinate, salicylanilide, domiphen bromide, delmopinol, octapinol and other piperidino derivatives, nicin preparations, chlorite salts; and mixtures of any of the foregoing.

1.64 Any of the preceding methods, wherein the oral care composition comprises an antioxidant, e.g., selected from the group consisting of Co-enzyme Q10, PQQ, Vitamin C, Vitamin E, Vitamin A, BHT, anethole-dithiothione, and mixtures thereof.

1.65 Any of the preceding methods, wherein the oral care composition comprises a whitening agent.

1.66 Any of the preceding methods, wherein the oral care composition comprises a whitening agent selected from a whitening active selected from the group consisting of peroxides, metal chlorites, perborates, percarbonates, peroxyacids, hypochlorites, and combinations thereof.

1.67 Any of the preceding methods, wherein the oral care composition further comprises hydrogen peroxide or a hydrogen peroxide source, e.g., urea peroxide or a peroxide salt or complex (e.g., such as peroxyphosphate, peroxycarbonate, perborate, peroxysilicate, or persulphate salts; for example calcium peroxyphosphate, sodium perborate, sodium carbonate peroxide, sodium peroxyphosphate, and potassium persulfate), or hydrogen peroxide polymer complexes such as hydrogen peroxide-polyvinyl pyrrolidone polymer complexes.

1.68 Any of the preceding methods, wherein the glycerin is in an amount from 20% -40% by wt. of the composition.

1.69 Any of the preceding methods, wherein the composition further comprises sorbitol.

1.70 The method of 1.69, wherein the sorbitol is from 10%-20% by wt. of the composition.

1.71 Any of the preceding methods, wherein the oral care composition further comprising an agent that interferes with or prevents bacterial attachment, e.g., ethyl lauroyl arginiate (ELA) or chitosan.

1.72 Any of the preceding methods, wherein the oral care composition comprises:
  a. about 1.0% zinc oxide
  b. about 0.5% zinc citrate
  c. about 1.5% L-arginine 1.73 Any of methods 1.0-1.71, wherein the oral care composition comprises:
  a. about 1.0% zinc oxide
  b. about 0.5% zinc citrate
  c. about 1.5% L-arginine
  d. about 0.32% sodium fluoride;
  e. about 35% glycerin;

1.74 Any of methods 1.0-1.71, wherein the oral care composition comprises:
  a. about 1.0% zinc oxide
  b. about 0.5% zinc citrate
  c. about 5% L-arginine
  d. about 0.32% sodium fluoride;
  e. about 26% glycerin; and
  f. about 13% sorbitol;
  Any of the preceding methods, wherein the method further comprises upon application of the oral care composition to the oral cavity, e.g., by rinsing, optionally in conjunction with brushing, a (i) reduction or inhibition of the formation of dental caries, (ii) reduction, repair or inhibition of pre-carious lesions of the enamel, e.g., as detected by quantitative light-induced fluorescence (QLF) or electrical caries measurement (ECM), (iii) reduction or inhibition of demineralization and promotion of remineralization of the teeth, (iv) reduction of hypersensitivity of the teeth, (v) reduction or inhibition of gingivitis, (vi) promotion of healing of sores or cuts in the mouth, (vii) reduction of levels of acid producing bacteria, (viii) increasing relative levels of arginolytic bacteria, (ix) inhibition of microbial biofilm formation in the oral cavity, (x) raising and/or maintaining plaque pH at levels of at least pH 5.5 following sugar challenge, (xi) reduction of plaque accumulation, (xii) treating, relieving or reducing dry mouth, (xiii) cleaning the teeth and oral cavity (xiv) reducing erosion, (xv) preventing stains and/or whitening teeth, (xvi) immunizing the teeth against cariogenic bacteria; and/or (xvii) promoting systemic health, including cardiovascular health, e.g., by reducing potential for systemic infection via the oral tissues.

1.75 Any of the preceding methods, wherein the oral care composition may be any of the following oral compositions selected from the group consisting of: a toothpaste or a dentifrice, a mouthwash or a mouth rinse, a topical oral gel, and a denture cleanser.

1.76 Any of the preceding methods, wherein the oral care composition is in the form of a chewing gum.

A composition obtained or obtainable by combining the ingredients as set forth in any of Method 1.0 et seq.

A composition for use as set forth in any of Method 1.0, et seq.

In another embodiment, the invention relates to a method to identify candidate oral care composition that are useful to treat one or more symptoms of a gastric disorder in the oral cavity of a subject in need thereof. (Method 2)

In one aspect, Method 2 includes 2.1, which is a method to identify candidate oral care composition that are useful to treat one or more symptoms of a gastric disorder in the oral cavity of a subject in need thereof, wherein Method 2.1 comprises the steps of providing a first sample and a second sample, e.g., toothpaste slurries, wherein the first and second samples have the same initial calcium concentrations; contacting the first sample with a measured quantity of acidic substance, e.g., aqueous acids (i.e., 1% Citric Acid solution) to form a solution; contacting the first sample with a candidate oral care composition; determining whether the amount of calcium which is released; contacting the second sample with the measured quantity of acidic substance to form a solution; contacting the second sample with any of the compositions described in Method 1.0, et seq.; determining whether the calcium released in the second sample solution has changed, wherein the amount of calcium released, in the first sample, being less than or equal to that of the second sample indicates that the candidate oral care composition are useful to treat one or more symptoms of a gastric disorder in the oral cavity of a subject in need thereof.

In one aspect, the invention contemplates that a candidate oral care composition that is useful to treat one or more symptoms of a gastric disorder in the oral cavity of a subject in need thereof, is identified using the method of Method 2.1.

In one further aspect, Method 2.1 contemplates an embodiment where the first and second samples are added simultaneously with the acidic substance.

In one aspect, disclosed is an oral care composition (Composition 1.0) comprising:
a. Basic amino acid in free or salt form, wherein the basic amino acid is arginine (e.g., free form arginine);
b. zinc oxide and zinc citrate; and
c. an orally acceptable carrier;
wherein the composition inhibits calcium release when measured against a reference standard, as measured when challenged in an acid aqueous solution with citric acid in an amount of about 1% (w/w).

In a further aspect, Composition 1.0 can be any of the compositions as described in Method 1.0, et seq.

The invention further relates to a method to treat acid-related conditions in the oral cavity, comprising administering to a subject any of any of the compositions described in Method 1.0, et seq.

DETAILED DESCRIPTION

As used herein, the term "oral composition" means the total composition that is delivered to the oral surfaces. The composition is further defined as a product which, during the normal course of usage, is not, the purposes of systemic administration of particular therapeutic agents, intentionally swallowed but is rather retained in the oral cavity for a time sufficient to contact substantially all of the dental surfaces and/or oral tissues for the purposes of oral activity. Examples of such compositions include, but are not limited to, toothpaste or a dentifrice, a mouthwash or a mouth rinse, a topical oral gel, a denture cleanser, and the like.

As used herein, the term "dentifrice" means paste, gel, or liquid formulations unless otherwise specified. The dentifrice composition can be in any desired form such as deep striped, surface striped, multi-layered, having the gel surrounding the paste, or any combination thereof. Alternatively the oral composition may be dual phase dispensed from a separated compartment dispenser.

"Dental Erosion" or "Erosion of tooth enamel", as used herein, is defined as a loss of dental hard tissue caused by a chemical process (i.e., exposure to intrinsic acid (e.g., gastric acid)) that does not involve bacteria.

The word "effective amount" is intended to encompass a therapeutically effective amount to treat a specific disease or disorder or symptom.

The term "subject" includes human or non-human (i.e., animal) subjects or patients. In a particular embodiment, the invention encompasses both human and nonhuman subjects. In another embodiment, the invention encompasses nonhuman. In other embodiment, the term encompasses human.

The term "gastric acid" refers to gastric acid or stomach acid, wherein the gastric acid or stomach acid is a digestive fluid which is formed in the stomach, and is composed of hydrochloric acid, potassium chloride, and sodium chloride.

Unless otherwise specified, all percentages and amounts expressed herein and elsewhere in the specification should be understood to refer to percentages by weight. The amounts given are based on the active weight of the material.

Basic Amino Acids

The basic amino acids which can be used in the compositions and methods of the invention include not only naturally occurring basic amino acids, such as arginine, lysine, and histidine, but also any basic amino acids having a carboxyl group and an amino group in the molecule, which are water-soluble and provide an aqueous solution with a pH of 7 or greater.

Accordingly, basic amino acids include, but are not limited to, arginine, lysine, serine, citrulline, ornithine, creatine, histidine, diaminobutanoic acid, diaminoproprionic acid, salts thereof or combinations thereof. In a particular embodiment, the basic amino acids are selected from arginine, citrulline, and ornithine.

In certain embodiments, the basic amino acid is arginine, for example, L-arginine, or a salt thereof.

The compositions of the invention (e.g., compositions described in Method 1.0 et seq) are intended for topical use in the mouth and so salts for use in the present invention should be safe for such use, in the amounts and concentrations provided. Suitable salts include salts known in the art to be pharmaceutically acceptable salts are generally considered to be physiologically acceptable in the amounts and concentrations provided. Physiologically acceptable salts include those derived from pharmaceutically acceptable inorganic or organic acids or bases, for example acid addition salts formed by acids which form a physiological acceptable anion, e.g., hydrochloride or bromide salt, and base addition salts formed by bases which form a physiologically acceptable cation, for example those derived from alkali metals such as potassium and sodium or alkaline earth metals such as calcium and magnesium. Physiologically acceptable salts may be obtained using standard procedures known in the art, for example, by reacting a sufficiently basic compound such as an amine with a suitable acid affording a physiologically acceptable anion.

Fluoride Ion Source

The oral care compositions (e.g., compositions described in Method 1.0 et seq) may further include one or more fluoride ion sources, e.g., soluble fluoride salts. A wide variety of fluoride ion-yielding materials can be employed as sources of soluble fluoride in the present compositions. Examples of suitable fluoride ion-yielding materials are found in U.S. Pat. No. 3,535,421, to Briner et al.; U.S. Pat. No. 4,885,155, to Parran, Jr. et al. and U.S. Pat. No. 3,678,154, to Widder et al., each of which are incorporated herein by reference. Representative fluoride ion sources used with the present invention (e.g., compositions described in Method 1.0 et seq.) include, but are not limited to, stannous fluoride, sodium fluoride, potassium fluoride, sodium monofluorophosphate, sodium fluorosilicate, ammonium fluorosilicate, amine fluoride, ammonium fluoride, and combinations thereof. In certain embodiments the fluoride ion source includes stannous fluoride, sodium fluoride, sodium monofluorophosphate as well as mixtures thereof. Where the formulation comprises calcium salts, the fluoride salts are preferably salts wherein the fluoride is covalently bound to another atom, e.g., as in sodium monofluorophosphate, rather than merely ionically bound, e.g., as in sodium fluoride.

Surfactants

The invention may in some embodiments contain anionic surfactants, e.g., e.g., compositions described in Method 1.0 et seq, for example, water-soluble salts of higher fatty acid monoglyceride monosulfates, such as the sodium salt of the monosulfated monoglyceride of hydrogenated coconut oil fatty acids such as sodium N-methyl N-cocoyl taurate, sodium cocomo-glyceride sulfate; higher alkyl sulfates, such as sodium lauryl sulfate; higher alkyl-ether sulfates, e.g., of formula $CH_3(CH_2)_m CH_2(OCH_2CH_2)_n OSO_3 X$, wherein m is 6-16, e.g., 10, n is 1-6, e.g., 2, 3 or 4, and X is Na or, for example sodium laureth-2 sulfate $(CH_3(CH_2)_{10}CH_2(OCH_2CH_2)_2 OSO_3 Na)$; higher alkyl aryl sulfonates such as sodium dodecyl benzene sulfonate (sodium lauryl benzene sulfonate); higher alkyl sulfoacetates, such as sodium lauryl sulfoacetate (dodecyl sodium sulfoacetate), higher fatty acid esters of 1,2 dihydroxy propane sulfonate, sulfocolaurate (N-2-ethyl laurate potassium sulfoacetamide) and sodium lauryl sarcosinate. By "higher alkyl" is meant, e.g., $C_{6-30}$ alkyl. In particular embodiments, the anionic surfactant (where present) is selected from sodium lauryl sulfate and sodium ether lauryl sulfate. When present, the anionic surfactant is present in an amount which is effective, e.g., >0.001% by weight of the formulation, but not at a concentration which would be irritating to the oral tissue, e.g., 1%, and optimal concentrations depend on the particular formulation and the particular surfactant. In one embodiment, the anionic surfactant is present at from 0.03% to 5% by weight, e.g., 1.5%.

In another embodiment, cationic surfactants useful in the present invention can be broadly defined as derivatives of aliphatic quaternary ammonium compounds having one long alkyl chain containing 8 to 18 carbon atoms such as lauryl trimethylammonium chloride, cetyl pyridinium chloride, cetyl trimethylammonium bromide, di-isobutylphenoxyethyldimethylbenzylammonium chloride, coconut alkyltrimethylammonium nitrite, cetyl pyridinium fluoride, and mixtures thereof. Illustrative cationic surfactants are the quaternary ammonium fluorides described in U.S. Pat. No. 3,535,421, to Briner et al., herein incorporated by reference. Certain cationic surfactants can also act as germicides in the compositions.

Illustrative nonionic surfactants of compositions described in Method 1.0, et seq., that can be used in the compositions of the invention can be broadly defined as compounds produced by the condensation of alkylene oxide groups (hydrophilic in nature) with an organic hydrophobic compound which may be aliphatic or alkylaromatic in nature. Examples of suitable nonionic surfactants include, but are not limited to, the Pluronics, polyethylene oxide condensates of alkyl phenols, products derived from the condensation of ethylene oxide with the reaction product of propylene oxide and ethylene diamine, ethylene oxide condensates of aliphatic alcohols, long chain tertiary amine oxides, long chain tertiary phosphine oxides, long chain dialkyl sulfoxides and mixtures of such materials. In a particular embodiment, the composition of the invention comprises a nonionic surfactant selected from poloxamers (e.g., poloxamer 407), polysorbates (e.g., polysorbate 20), polyoxyl hydrogenated castor oils (e.g., polyoxyl 40 hydrogenated castor oil), and mixtures thereof.

Illustrative amphoteric surfactants of compositions described in Method 1.0, et seq., that can be used in the compositions of the invention include betaines (such as cocamidopropylbetaine), derivatives of aliphatic secondary and tertiary amines in which the aliphatic radical can be a straight or branched chain and wherein one of the aliphatic substituents contains about 8-18 carbon atoms and one contains an anionic water-solubilizing group (such as carboxylate, sulfonate, sulfate, phosphate or phosphonate), and mixtures of such materials.

The surfactant or mixtures of compatible surfactants can be present in the compositions of the present invention (e.g., compositions described in Method 1.0 et seq) in 0.1% to 5%, in another embodiment 0.3% to 3% and in another embodiment 0.5% to 2% by weight of the total composition.

Flavoring Agents

The oral care compositions of the invention may also include a flavoring agent. Flavoring agents which are used in the practice of the present invention include, but are not limited to, essential oils and various flavoring aldehydes, esters, alcohols, and similar materials, as well as sweeteners such as sodium saccharin. Examples of the essential oils include oils of spearmint, peppermint, wintergreen, sassafras, clove, sage, eucalyptus, marjoram, cinnamon, lemon, lime, grapefruit, and orange. Also useful are such chemicals as menthol, carvone, and anethole. Certain embodiments employ the oils of peppermint and spearmint.

The flavoring agent is incorporated in the oral composition (e.g., compositions described in Method 1.0, et seq) at a concentration of 0.01 to 2% by weight.

Chelating and Anti-Calculus Agents

The oral care compositions of the invention also may include one or more chelating agents able to complex calcium found in the cell walls of the bacteria. Binding of this calcium weakens the bacterial cell wall and augments bacterial lysis.

Another group of agents suitable for use as chelating or anti-calculus agents in the present invention are the soluble pyrophosphates. The pyrophosphate salts used in the present compositions can be any of the alkali metal pyrophosphate salts. In certain embodiments, salts include tetra alkali metal pyrophosphate, dialkali metal diacid pyrophosphate, trialkali metal monoacid pyrophosphate and mixtures thereof, wherein the alkali metals are sodium or potassium. The salts are useful in both their hydrated and unhydrated forms. An effective amount of pyrophosphate salt useful in the present composition is generally enough to provide least 0.1 wt. % pyrophosphate ions, e.g., 0.1 to 3 wt 5, e.g., 0.1 to 2 wt %, e.g., 0.1 to 1 wt %, e.g., 0.2 to 0.5 wt %. The pyrophosphates also contribute to preservation of the compositions by lowering water activity.

Polymers

The oral care compositions of the invention also optionally include one or more polymers, such as polyethylene glycols, polyvinyl methyl ether maleic acid copolymers, polysaccharides (e.g., cellulose derivatives, for example carboxymethyl cellulose, or polysaccharide gums, for example xanthan gum or carrageenan gum). Acidic polymers, for example polyacrylate gels, may be provided in the form of their free acids or partially or fully neutralized water soluble alkali metal (e.g., potassium and sodium) or ammonium salts. Certain embodiments include 1:4 to 4:1 copolymers of maleic anhydride or acid with another polymerizable ethylenically unsaturated monomer, for example, methyl vinyl ether (methoxyethylene) having a molecular weight (M.W.) of about 30,000 to about 1,000,000. These copolymers are available for example as Gantrez AN 139 (M.W. 500,000), AN 1 19 (M.W. 250,000) and S-97 Pharmaceutical Grade (M.W. 70,000), of GAF Chemicals Corporation.

Other operative polymers include those such as the 1:1 copolymers of maleic anhydride with ethyl acrylate, hydroxyethyl methacrylate, N-vinyl-2-pyrollidone, or ethylene, the latter being available for example as Monsanto EMA No. 1 103, M.W. 10,000 and EMA Grade 61, and 1:1 copolymers of acrylic acid with methyl or hydroxyethyl methacrylate, methyl or ethyl acrylate, isobutyl vinyl ether or N-vinyl-2-pyrrolidone.

Suitable generally, are polymerized olefinically or ethylenically unsaturated carboxylic acids containing an activated carbon-to-carbon olefinic double bond and at least one carboxyl group, that is, an acid containing an olefinic double bond which readily functions in polymerization because of its presence in the monomer molecule either in the alpha-beta position with respect to a carboxyl group or as part of a terminal methylene grouping. Illustrative of such acids are acrylic, methacrylic, ethacrylic, alpha-chloroacrylic, crotonic, beta-acryloxy propionic, sorbic, alpha-chlorsorbic, cinnamic, beta-styrylacrylic, muconic, itaconic, citraconic, mesaconic, glutaconic, aconitic, alpha-phenylacrylic, 2-benzyl acrylic, 2-cyclohexylacrylic, angelic, umbellic, fumaric, maleic acids and anhydrides. Other different olefinic monomers copolymerizable with such carboxylic monomers include vinylacetate, vinyl chloride, dimethyl maleate and the like. Copolymers contain sufficient carboxylic salt groups for water-solubility.

A further class of polymeric agents includes a composition containing homopolymers of substituted acrylamides and/or homopolymers of unsaturated sulfonic acids and salts thereof, in particular where polymers are based on unsaturated sulfonic acids selected from acrylamidoalkane sulfonic acids such as 2-acrylamide 2 methylpropane sulfonic acid having a molecular weight of about 1,000 to about 2,000, 000, described in U.S. Pat. No. 4,842,847, Jun. 27, 1989 to Zahid, incorporated herein by reference.

Another useful class of polymeric agents includes polyamino acids, particularly those containing proportions of anionic surface-active amino acids such as aspartic acid, glutamic acid and phosphoserine, as disclosed in U.S. Pat. No. 4,866,161 Sikes et al., incorporated herein by reference.

In preparing oral care compositions, it is sometimes necessary to add some thickening material to provide a desirable consistency or to stabilize or enhance the performance of the formulation. In certain embodiments, the thickening agents are carboxyvinyl polymers, carrageenan, xanthan gum, hydroxyethyl cellulose and water soluble salts of cellulose ethers such as sodium carboxymethyl cellulose and sodium carboxymethyl hydroxyethyl cellulose. Natural gums such as karaya, gum arabic, and gum tragacanth can also be incorporated. Colloidal magnesium aluminum silicate or finely divided silica can be used as component of the thickening composition to further improve the composition's texture. In certain embodiments, thickening agents in an amount of about 0.5% to about 5.0% by weight of the total composition are used.

Abrasives

Natural calcium carbonate is found in rocks such as chalk, limestone, marble and travertine. It is also the principle component of egg shells and the shells of mollusks. The natural calcium carbonate abrasive of the invention is typically a finely ground limestone which may optionally be refined or partially refined to remove impurities. For use in the present invention, the material has an average particle size of less than 10 microns, e.g., 3-7 microns, e.g. about 5.5 microns. For example, a small particle silica may have an average particle size (D50) of 2.5-4.5 microns. Because natural calcium carbonate may contain a high proportion of relatively large particles of not carefully controlled, which may unacceptably increase the abrasivity, preferably no more than 0.01%, preferably no more than 0.004% by weight of particles would not pass through a 325 mesh. The material has strong crystal structure, and is thus much harder and more abrasive than precipitated calcium carbonate. The tap density for the natural calcium carbonate is for example between 1 and 1.5 g/cc, e.g., about 1.2 for example about 1.19 g/cc. There are different polymorphs of natural calcium carbonate, e.g., calcite, aragonite and vaterite, calcite being preferred for purposes of this invention. An example of a commercially available product suitable for use in the present invention includes Vicron ® 25-11 FG from GMZ.

Precipitated calcium carbonate is generally made by calcining limestone, to make calcium oxide (lime), which can then be converted back to calcium carbonate by reaction with carbon dioxide in water. Precipitated calcium carbonate has a different crystal structure from natural calcium carbonate. It is generally more friable and more porous, thus having lower abrasivity and higher water absorption. For use in the present invention, the particles are small, e.g., having an average particle size of 1-5 microns, and e.g., no more than 0.1%, preferably no more than 0.05% by weight of particles which would not pass through a 325 mesh. The particles may for example have a D50 of 3-6 microns, for example 3.8=4.9, e.g., about 4.3; a D50 of 1-4 microns, e.g. 2.2-2.6 microns, e.g., about 2.4 microns, and a D10 of 1-2 microns, e.g., 1.2-1.4, e.g. about 1.3 microns. The particles have relatively high water absorption, e.g., at least 25 g/100 g, e.g. 30-70 g/100 g. Examples of commercially available products suitable for use in the present invention include, for example, Carbolag® 15 Plus from Lagos Industria Quimica.

In certain embodiments the invention may comprise additional calcium-containing abrasives, for example calcium phosphate abrasive, e.g., tricalcium phosphate ($Ca_3(PO_4)_2$), hydroxyapatite ($Ca_{10}(PO_4)_6(OH)_2$), or dicalcium phosphate dihydrate ($CaHPO_4 \cdot 2H_2O$, also sometimes referred to herein as DiCal) or calcium pyrophosphate, and/or silica abrasives, sodium metaphosphate, potassium metaphosphate, aluminum silicate, calcined alumina, bentonite or other siliceous materials, or combinations thereof. Any silica suitable for oral care compositions may be used, such as precipitated silicas or silica gels. For example synthetic amorphous silica. Silica may also be available as a thickening agent, e.g., particle silica. For example, the silica can also be small particle silica (e.g., Sorbosil AC43 from PQ Corporation, Warrington, United Kingdom). However the additional abrasives are preferably not present in a type or amount so as to increase the RDA of the dentifrice to levels which could damage sensitive teeth, e.g., greater than 130.

Water

Water is present in the oral compositions of the invention. Water, employed in the preparation of commercial oral compositions should be deionized and free of organic impurities. Water commonly makes up the balance of the compositions and includes 5% to 45%, e.g., 10% to 20%, e.g., 25-35%, by weight of the oral compositions. This amount of water includes the free water which is added plus that amount which is introduced with other materials such as with sorbitol or silica or any components of the invention. The Karl Fischer method is a one measure of calculating free water.

Humectants

Within certain embodiments of the oral compositions, it is also desirable to incorporate a further humectant (e.g., in addition to glycerin) to reduce evaporation and also contribute towards preservation by lowering water activity. Certain humectants can also impart desirable sweetness or flavor to the compositions. The humectant, on a pure humectant basis, generally includes 15% to 70% in one embodiment or 30% to 65% in another embodiment by weight of the composition.

Suitable humectants include edible polyhydric alcohols such as glycerin, sorbitol, xylitol, propylene glycol as well as other polyols and mixtures of these humectants. Mixtures of glycerine and sorbitol may be used in certain embodiments as the humectant component of the compositions herein (e.g., compositions described in Method 1.0 et seq).

The present invention in its method aspect involves applying to the oral cavity a safe and effective amount of the compositions described herein.

The compositions and methods according to the invention (e.g., compositions described in Method 1.0, et seq) can be incorporated into oral compositions for the care of the mouth and teeth such as toothpastes, transparent pastes, gels, mouth rinses, sprays and chewing gum.

As used throughout, ranges are used as shorthand for describing each and every value that is within the range. Any value within the range can be selected as the terminus of the range. In addition, all references cited herein are hereby incorporated by reference in their entireties. In the event of a conflict in a definition in the present disclosure and that of a cited reference, the present disclosure controls. It is understood that when formulations are described, they may be described in terms of their ingredients, as is common in the art, notwithstanding that these ingredients may react with one another in the actual formulation as it is made, stored and used, and such products are intended to be covered by the formulations described.

Unless otherwise specified, all percentages and amounts expressed herein and elsewhere in the specification should be understood to refer to percentages by weight. The amounts given are based on the active weight of the material.

The following examples further describe and demonstrate illustrative embodiments within the scope of the present invention. The examples are given solely for illustration and are not to be construed as limitations of this invention as many variations are possible without departing from the spirit and scope thereof. Various modifications of the invention in addition to those shown and described herein should be apparent to those skilled in the art and are intended to fall within the appended claims.

EXAMPLES

Example 1

Preparation of Demineralization and Treatment Solutions

An aqueous 1% (w/w) citric acid stock solution is prepared by dissolving anhydrous citric acid powder in deionized water with stirring at room temperature. The acidity is adjusted to pH 3.8 with 1M NaOH Additional deionized water is added to a total mass of 1000 g (pH 3.77). Dentifrice slurries (1:2) are generated by suspending the indicated dentifrice and deionized water followed by speed mixing for 2 minutes. Three separate slurries are generated for each toothpaste to permit three separate replicates for each toothpaste dose tested.

Demineralization Procedure:

Toothpaste slurry (at the indicated amounts, Table 1) was added to 0.2 g of calcium deficient carbonated hydroxyapatite (HA) powder (Himed) massed into a 14 mL culture tube. Calcium-deficient HA powder is chosen as the mimic calcium-phosphate material given its similarity in structure and elemental composition to dental enamel. Citric acid (as indicated) is immediately added sequentially. The resultant suspensions are mixed on an orbital shaker for 1 hour. Samples are then centrifuged at 4000 rpm for 5 minutes to pellet the HA powder. The pH of the supernatant is obtained and a portion of the supernatant (1 mL) is removed for elemental analysis. To prepare the samples for analytical analysis, the supernatant aliquot (1 mL) is combined with concentrated nitric acid (1 mL) for 10 minutes. The whole solution is then diluted to a total volume of 10 mL with DI water. Samples are ether filtered or centrifuged to remove residual insoluble material.

TABLE 1

Experimental setup depicting ratios of demineralization solution and toothpaste slurry for incubation with HA powder.

| Dilution Factor of 1:2 Slurry | Toothpaste Slurry (1:2), µL | Demineralization Solution (µL) |
|---|---|---|
| 4 | 5000 | 5000 |
| 8 | 2500 | 7500 |
| 20 | 1000 | 9000 |
| 40 | 500 | 9500 |
| 80 | 250 | 9750 |

Method Validation: To validate the method, the effect on calcium release for a no fluoride dentifrice ("Negative Control") is compared to a commercially available dentifrice. Here, the commercially-available dentifrice ("Positive control") contains 0.3% triclosan, 2% PVM/MA copolymer, and 1450 ppm F as sodium fluoride in a silica base. The Positive Control does not contain zinc. As a function of toothpaste dilution factor, the fluoride effect in prevention of calcium release is clear from Table 2. The no fluoride toothpaste shows no dose response while the fluoride toothpaste showed characteristic calcium release dependent upon the toothpaste dilution factor.

TABLE 2

| Toothpaste Dilution Factor | Negative Control (Calcium Released (ppm)) | Positive Control Calcium Released (ppm) |
|---|---|---|
| 4 | 1014 ± 82 | 94 ± 15 |
| 8 | 1165 ± 77 | 126 ± 4 |
| 20 | 1125 ± 146 | 198 ± 11 |
| 40 | 1151 ± 118 | 247 ± 13 |
| 80 | 991 ± 76 | 331 ± 53 |

Example 2

The present example illustrates that zinc toothpaste inhibits calcium release beyond any fluoride effects. Discernible differences are observed in the amount of calcium released between:

a.) Toothpaste slurries of the Test Formulation containing 1% zinc oxide, 0.5% zinc citrate trihydrate, 1.5% L-arginine, and 1450 ppm sodium fluoride in a silica base; and b.) Toothpaste slurries of the Positive Control (i.e., the commercial product) containing 0.3% triclosan, 2% PVM/MA copolymer, and 1450 ppm F as sodium fluoride in a silica base.

Here, prevention of calcium release was similar between the Test Formulation and Positive Control at high concentrations of the toothpaste slurry. However, at dilute concentrations (less than or equal to 150 ppm Zn), the Test Formulation demonstrates less calcium release as a function of toothpaste dilution factor in comparison to the Positive Control. Fluoride levels are equal in both the Test Formulation and Positive Control. Therefore, this data suggests that the active materials in the zinc formulas (i.e., Test Formulation) are having an effect on the amount of calcium released.

TABLE 3

| Toothpaste Dilution Factor | Positive Control (Calcium Released (ppm)) | Test Formulation Calcium Released (ppm) |
|---|---|---|
| 4 | 94 ± 15 | 112 ± 2 |
| 8 | 126 ± 4 | 120 ± 1 |
| 20 | 198 ± 11 | 184 ± 10 |
| 40 | 247 ± 13 | 190 ± 20 |
| 80 | 331 ± 53 | 233 ± 6 |

Example 3

The amount of zinc remaining in the solution is further measured by ICP analysis. A direct logarithmic correlation is observed between the calcium released and the concentration of zinc in the demineralization solution. Even at the lowest level of zinc (56 ppm) only approximately 230 ppm calcium is released with Test Formulations, a about a 30% improvement over the Positive control. Results are seen in Tables 5 and 6.

TABLE 4

Positive Control

| Toothpaste Dilution Factor | Zinc (ppm) | Calcium Released (ppm) |
|---|---|---|
| 4 | 0 | 94 ± 15 |
| 8 | 0 | 126 ± 4 |
| 20 | 0 | 198 ± 11 |
| 40 | 0 | 247 ± 13 |
| 80 | 0 | 331 ± 53 |

TABLE 5

Test Formulation

| Toothpaste Dilution Factor | Zinc (ppm) | Calcium Released (ppm) |
|---|---|---|
| 4 | 1240 ± 17 | 112 ± 2 |
| 8 | 735 ± 87 | 120 ± 1 |
| 20 | 351 ± 14 | 184 ± 10 |
| 40 | 140 ± 20 | 190 ± 20 |
| 80 | 56 ± 2 | 233 ± 6 |

Example 4

Representative Dentifrice Formulation

Representative Dentifrice Formulation:

| Ingredient | Formula 1 |
|---|---|
| DEMINERALIZED WATER | Q.S. |
| ABRASIVES | 10%-20% |
| 99.0%-101.0% GLYCERIN - USP, EP VEG | 35 |
| L-Arginine | 1.5 |
| AMPHOTERIC SURFACTANT | 1.0%-1.5% |
| NON-IONIC SURFACTANT | 0.25%-0.75% |
| POLYMERS | 0.75%-1.5% |
| ALKALI PHOSPHATE SALT | 0.25%-0.75% |
| ZINC CITRATE TRIHYDRATE | 0.5 |
| WHITENING AGENT | 0.25%-1.0% |
| FLAVORING AGENTS | 1.5%-1.9% |

-continued

| Ingredient | Formula 1 |
|---|---|
| 85% SYRUPY PHOSPHORIC ACID - FOOD GRADE | 0-0.35 |
| SODIUM FLUORIDE - USP, EP | 0.32 |
| SILICA - THICKENER | 5%-7% |
| ANIONIC SURFACTANT | 1%-3% |
| ZINC OXIDE | 1 |
| PRESERVATIVE | 0.4 |
| Total Components | 100 |

Example 5

Representative Control Formulation

The following is a representative negative control dentifrice formulation for use in the described examples, wherein the negative control formulation does not contain fluoride:

| Ingredient | Formula 1 |
|---|---|
| DEMINERALIZED WATER | Q.S. |
| ABRASIVES | 7%-9% |
| Sorbitol - Non Crystal - 70% Solution | 65%-70% |
| AMPHOTERIC SURFACTANT | 1.0%-1.5% |
| NON-IONIC SURFACTANT | 0.25%-0.75% |
| POLYMERS | 0.75%-1.5% |
| WHITENING AGENT | 0.25%-1.0% |
| FLAVORING AGENTS | 1.0%-1.5% |
| 85% SYRUPY PHOSPHORIC ACID - FOOD GRADE | 0-0.35 |
| SILICA - THICKENER | 6%-9% |
| ANIONIC SURFACTANT | 1%-3% |
| Total Components | 100 |

Example 6

Gastric Acid Simulation

Preparation of Demineralization and Treatment Solutions

An aqueous artificial gastric acid stock solution is prepared by dissolving sodium chloride (5 g), potassium chloride (5 g), and HCl (12M, 5 g) in deionized water with stirring at room temperature. The acidity is adjusted to pH 3 with 1M NaOH. Additional deionized water was added to a total mass of 1000 g (pH 3.11). This experiment is meant to simulate conditions where enamel in the oral cavity is exposed to gastric acid.

Dentifrice slurries (1:2) are generated by suspending the indicated dentifrice (5 g) and deionized water (10 g) followed by speed mixing for 2 minutes. Five separate slurries are generated for each toothpaste to permit five separate replicates for each toothpaste dose tested.

Demineralization Procedure

Toothpaste slurry (at the indicated amounts, Table 6) are added to 0.2 g of calcium deficient carbonated hydroxyapatite (HA) powder massed into a 14 mL culture tube. Calcium-deficient HA powder is chosen as the mimic calcium-phosphate material given its similarity in structure and elemental composition to dental enamel artificial gastric acid (as indicated) is immediately added sequentially. The resultant suspensions are mixed on an orbital shaker for 1 hour. Samples are then centrifuged at 4000 rpm for 5 minutes to pellet the HA powder. To prepare the samples for analytical analysis, the supernatant aliquot (1 mL) was combined with concentrated nitric acid (0.5 mL) for 10 minutes. The whole solution is then diluted to a total volume of 5 mL with DI water.

TABLE 6

Experimental setup depicting ratios of demineralization solution and toothpaste slurry for incubation with HA powder.

| Dilution Factor of 1:2 slurry | Toothpaste Slurry (1:2), uL | Artificial Gastric Acid, uL |
|---|---|---|
| 40 | 500 | 9500 |
| 80 | 250 | 9750 |
| 125 | 160 | 9840 |

Significant differences in the prevention of calcium release are observed between test formulations and the positive control at extremely low concentrations of toothpaste slurry (e.g., 80- and 125-fold dilution). Without being bound by theory, this level of dilution may be relevant given the amount of toothpaste that would remain in the mouth after brushing. A directional benefit in the prevention of calcium release was observed with test formulations at 40-fold toothpaste dilution in comparison to the positive controls. All toothpastes containing fluoride were shown to perform significantly better against the prevention of calcium release in comparison to water and the negative control with 0 ppm fluoride.

With all fluoride levels being equal in each formula, this data would suggest that the active materials in the Test Formulation are having an effect on the amount of calcium released, i.e., at very low concentrations of toothpaste slurry. Therefore, this data suggests that the active materials in the Test Formulation are having an effect on the amount of calcium released from hydroxyapatite upon exposure to gastric acid like solution.

TABLE 7

The amount of calcium released by hydroxyapatite upon exposure to an artificial gastric acid solution. Note that values which do not share a common letter, i.e., "A" or "B" or "C", demonstrate statistically significant differences.

| Dilution Factor of 1:2 slurry | Test Formulation Calcium Released (ppm) | | Positive Control (Calcium Released (ppm)) | | Negative Control (Calcium Released (ppm)) | | Water | |
|---|---|---|---|---|---|---|---|---|
| 40 | 9.35 ± 0.90 | A | 12.48 ± 1.59 | A | 25.07 ± 2.99 | B | 25.37 ± 1.34 | B |
| 80 | 10.94 ± 0.68 | A | 16.53 ± 3.80 | B | 24.98 ± 2.02 | C | 27.94 ± 0.85 | C |
| 125 | 14.38 ± 1.06 | A | 17.97 ± 1.11 | B | 26.02 ± 1.01 | C | 26.76 0.54 | C |

The "Test Formulation" and "Positive Control" and "Negative Control" mentioned in Table 7 refer to the following:

a. Toothpaste slurries of the Test Formulation containing 1% zinc oxide, 0.5% zinc citrate trihydrate, 1.5% L-arginine, and 1450 ppm sodium fluoride in a silica base; and b. Toothpaste slurries of the Positive Control (i.e., the commercial product) containing 0.3% triclosan, 2% PVM/MA copolymer, and 1450 ppm F as sodium fluoride in a silica base.

c. Toothpaste slurries of the Negative Control are as described in Example 5 above.

While particular embodiments of the invention have been illustrated and described, it will be obvious to those skilled in the art that various changes and modifications may be made without departing from the scope of the invention as defined in the appended claims.

What is claimed is:

1. A method of treating one or more symptoms of a gastric disorder in the oral cavity of a subject in need thereof, wherein the method comprises applying to the subject's teeth an oral care composition comprising:
    a. a basic amino acid in free or salt form, wherein the basic amino acid is arginine in an amount from 0.1 wt % to 6.0 wt %;
    b. zinc oxide and zinc citrate, wherein the zinc oxide is present in an amount from 0.75% by wt. to 1.25% by wt. and the zinc citrate is present in an amount from 0.25% by wt. to 1.0% by wt;
    c. an orally acceptable carrier;
wherein the gastric disorder is gastroesophageal reflux disease (GERD); and
wherein the one or more symptoms of the gastric disorder comprise dental erosion due to loss of calcium in the subject's tooth enamel consequent to the presence of gastric acid in the oral cavity.

2. The method according to claim 1, wherein the oral care composition inhibits or decreases the release of calcium from the subject's tooth enamel.

3. The method according to claim 2, wherein the inhibition or decrease of the release of calcium in the subject's tooth enamel is relative to a reference standard.

4. The method according to claim 1, wherein the oral care composition inhibits the release of calcium relative to one or more compositions that do not contain zinc.

5. The method according to claim 1, wherein the one or more symptoms is that the subject is exposed to gastric acids in the oral cavity during sleep.

6. The method according to claim 1, wherein the subject is at risk for dental erosion.

7. The method according to claim 6, wherein the risk for dental erosion is selected from the group consisting of: xerostomia, tooth hypersensitivity, weakened tooth integrity, and tooth discoloration.

8. The method according to claim 1, wherein the oral care composition comprises:
    a. about 1.0% zinc oxide,
    b. about 0.5% zinc citrate, and
    c. about 1.5% L-arginine.

* * * * *